(12) United States Patent
Cull

(10) Patent No.: US 10,869,777 B2
(45) Date of Patent: Dec. 22, 2020

(54) TREATING MEDICAL CONDITIONS IN BODY CAVITIES

(76) Inventor: Kimberly Cull, Columbus, OH (US)

( * ) Notice: Subject to any disclaimer, the term of this patent is extended or adjusted under 35 U.S.C. 154(b) by 0 days.

(21) Appl. No.: 13/637,496

(22) PCT Filed: Mar. 25, 2011

(86) PCT No.: PCT/US2011/030052
§ 371 (c)(1),
(2), (4) Date: Sep. 26, 2012

(87) PCT Pub. No.: WO2011/123362
PCT Pub. Date: Oct. 6, 2011

(65) Prior Publication Data
US 2013/0023970 A1  Jan. 24, 2013

Related U.S. Application Data

(60) Provisional application No. 61/318,339, filed on Mar. 28, 2010.

(51) Int. Cl.
| A61F 7/12 | (2006.01) |
| A61F 7/10 | (2006.01) |
| A61F 7/00 | (2006.01) |
| A61F 7/02 | (2006.01) |

(52) U.S. Cl.
CPC .............. *A61F 7/12* (2013.01); *A61F 7/10* (2013.01); *A61F 7/106* (2013.01); *A61F 2007/005* (2013.01); *A61F 2007/0028* (2013.01); *A61F 2007/0276* (2013.01); *A61F 2007/108* (2013.01)

(58) Field of Classification Search
CPC .......... A61F 2007/108; A61F 2007/105; A61F 2007/101; A61F 2007/005; A61F 2007/0276; A61F 7/106; A61F 7/12; A61M 31/00; A61B 2017/4216
USPC .......................................... 607/138, 113, 116
See application file for complete search history.

(56) References Cited

U.S. PATENT DOCUMENTS

| 612,724 | A | * | 10/1898 | Hamilton ....................... 606/192 |
| 969,134 | A | * | 8/1910 | Cowie ....................... A61F 7/12 604/113 |
| 3,121,427 | A | * | 2/1964 | Mosier .......................... 604/368 |
| 3,893,834 | A | * | 7/1975 | Armstrong ........................... 62/4 |
| 3,939,842 | A | * | 2/1976 | Harris ................... A61F 5/0093 607/113 |
| 4,049,408 | A | * | 9/1977 | Patel .................................. 62/4 |
| 4,198,976 | A | * | 4/1980 | Drobish .................... A61F 6/08 128/832 |

(Continued)

*Primary Examiner* — Kaitlyn E Smith
*Assistant Examiner* — Yasamin Ekrami
(74) *Attorney, Agent, or Firm* — Plant & Planet Law Firm

(57) ABSTRACT

A device and method to treat an overgrowth of yeast in a body cavity and inflammatory and/or hemorrhagic conditions of a body cavity. The device comprising a shell, removal means, and a freezable filler contained in a chamber within the shell. When the filler is frozen and the device inserted into the body cavity, the shell cools the body cavity to a temperature that inhibits the replication of yeast and provides relief to symptoms. An external cooling component extending from the shell provides cooling at the body cavity opening. An expandable bladder in the shell provides tamponade treatment for body cavity hemorrhaging.

2 Claims, 4 Drawing Sheets

(56) References Cited

U.S. PATENT DOCUMENTS

| | | | | |
|---|---|---|---|---|
| 4,563,182 A * | 1/1986 | Stoy | A61F 5/0093 | |
| | | | 424/436 | |
| 4,605,006 A * | 8/1986 | Jacques | 607/113 | |
| 4,669,478 A * | 6/1987 | Robertson | A61F 6/08 | |
| | | | 600/300 | |
| 4,823,812 A * | 4/1989 | Eshel et al. | 607/156 | |
| 4,844,073 A * | 7/1989 | Pohler | A61F 7/12 | |
| | | | 607/113 | |
| 4,936,319 A * | 6/1990 | Neubardt | 128/849 | |
| 4,981,135 A * | 1/1991 | Hardy | 607/108 | |
| 5,062,425 A * | 11/1991 | Tucker | A61F 7/123 | |
| | | | 604/103.11 | |
| 5,086,786 A * | 2/1992 | Sogawa et al. | 607/115 | |
| 5,216,900 A * | 6/1993 | Jones | 62/457.2 | |
| 5,887,437 A * | 3/1999 | Maxim | 62/4 | |
| 6,139,486 A * | 10/2000 | Matuszewski et al. | 600/15 | |
| 6,440,160 B1 * | 8/2002 | Cordani et al. | 607/114 | |
| 6,648,909 B2 * | 11/2003 | Helming | 607/108 | |
| 6,893,419 B2 * | 5/2005 | Noda | A61F 7/12 | |
| | | | 604/113 | |
| 2003/0032935 A1 * | 2/2003 | Damiano et al. | 604/403 | |
| 2005/0222169 A1 * | 10/2005 | Ahmad et al. | 514/254.07 | |
| 2005/0288660 A1 * | 12/2005 | Ryan | A61B 90/04 | |
| | | | 606/28 | |
| 2007/0021809 A1 * | 1/2007 | Cole et al. | 607/113 | |
| 2007/0207186 A1 * | 9/2007 | Scanlon et al. | 424/424 | |
| 2007/0225781 A1 * | 9/2007 | Saadat et al. | 607/105 | |
| 2007/0239110 A1 * | 10/2007 | Shah | A61M 25/1011 | |
| | | | 604/96.01 | |
| 2008/0071336 A1 * | 3/2008 | Merriman | 607/113 | |
| 2008/0086186 A1 * | 4/2008 | Takeda et al. | 607/105 | |
| 2008/0135217 A1 * | 6/2008 | Turovskiy | A61B 18/18 | |
| | | | 165/104.33 | |
| 2012/0053546 A1 * | 3/2012 | Fogg et al. | 604/367 | |
| 2012/0089212 A1 * | 4/2012 | Benda et al. | 607/108 | |

\* cited by examiner

TREATING MEDICAL CONDITIONS IN BODY CAVITIES

CROSS-REFERENCES TO RELATED APPLICATIONS

This patent application claims the benefit of provisional patent application Ser. No. 61/318,338, filed Mar. 28, 2010, hereby incorporated by reference.

FIELD OF THE INVENTION

The present invention relates to a device and method for treating symptoms caused by an overgrowth of yeast. The invention is a unique non-medicinal treatment device to cure a common female ailment, vaginitis.

BACKGROUND OF THE INVENTION

Vaginitis is an irritation and/or inflammation of the vagina that affects millions of women each year. Vaginal infections produce a variety of symptoms, such as discharge, itching, odor, irritation, painful urination or bleeding. While vaginitis can be caused by bacteria or protozoa, an overgrowth of yeast, which is normally on the skin and in body cavities, can become a problem when certain conditions are present. Some risk factors for the development of yeast vaginitis are additional moisture and heat, found in situations like sunbathing, swimming, exercise, sexual intercourse, oral sex, tight fitting pants, panty hose, non-cotton crotched underwear, or thongs. Antibiotics, oral steroids, immunosuppressed states, diabetes mellitus, urinary incontinence, and some medications (oral contraceptives) can predispose a woman to recurrent yeast vaginitis. Other causes of vaginitis may include vulvodynia and vestibulitis, conditions suspected to be caused by repetitive treatment with antifungal creams.

There are eighty-one varieties of yeast, three of which—*Candida albicans, Candida torulopsis*, and *Candida glabarata*—are common causes of yeast vaginitis. For the most common—*Candida albicans*—over-the-counter remedies now available will treat and cure this type of yeast only 80% of the time. Current treatment for *Candida torulopsis* and *Candida glabarata* is only by a prescription antifungal cream. All over-the-counter antifungal creams treat only one form of yeast vaginitis (*Candida albicans*).

The current treatment systems use medicine/drugs (either oral or topical) to treat the condition. The over-the-counter remedies only address one species of yeast (*Candida albicans*)—and there are two others which cause this condition (torulopsis and glabarata). There is no available over-the-counter treatment for these two yeast subtypes. Likewise, there are no over-the-counter treatments for other types of pathogens in the vagina like trichomonas, gonorrhea, chlamydia, herpes, gardnerella or any other yet to be identified pathogen. The current therapies require the use of creams/semisolids or oral tablets. When the drug melts in the vagina, it spills out onto the perineum and causes more itching and burning. These emulsions contain many synthetic chemicals and preservatives, which are known to be caustic and allergenic to human skin and mucous membranes. These chemicals, most notably methyl parabens, propylene glycols, cetyl alcohols, sodium lauryl sulfates are caustic to the skin, yet are used routinely in the current antifungal medicines and other therapies (which do nothing more than treat the 'itch' symptom).

Because the woman is confused by the claims of over-the-counter medications, she is often frustrated and her condition worsens until she either buys more irritating creams or visits her doctor. This often results in multiple visits to a physician and repetitive and unnecessary treatments because it is often assumed that the condition has not been adequately treated, when in fact, the treatment resulted in a secondary problem—most notably contact or chemical dermatitis. It is theorized that another condition known as vestiblitis/vulvodynia is often diagnosed in women who have suffered from multiple yeast infections, and one can't help but wonder whether it was the condition or the treatment which caused these chronic, debilitating problems. In essence, a secondary condition results from the treatment used to cure the initial condition and is debilitating and presently incurable. These secondary disorders (vestibulitis/vulvodynia) are unquestionably worse than the initial condition for which the woman sought to cure/treat in the first place.

Furthermore, existing creams add moisture to the vagina, which is counterproductive to curing the overgrowth of yeast. Yeast thrives on moisture and warmth. Yeast replication is sensitive to temperature. The optimum growth temperature for most pathogenic fungi is around 86° F. Yeast is dormant and will not grow below about 50° F., and grows only slowly at about 55° F.

Although current drugs do cure many yeast infections, they are not without significant side effects. Oral antifungal medicine also poses significant risks. Oral antifungals used to treat yeast vaginitis can be compared to using a "bazooka to shoot a mouse"; and, fluconazole only treats *Candida albicans*.

Additional problems exist with currently available treatments for vaginitis caused by yeast infections. Current medications, while effective, may take 3-7 days to provide relief. In addition, both oral and topical drugs may adversely interact with other medications, such as antihistamines, antidepressants, asthma medications and the like. Some topical medications can cause toxic skin reactions. Further, the success rate of existing treatment methods range from 60-80% because a chosen drug may not be effective against each of the strains of *Candida*. A need exists for a method of treating vaginitis caused by yeast infections that is immediate, non-invasive, inert and effective against all yeasts.

In addition, body cavity hemorrhaging and inflammation is a common problem. Vaginal hemorrhaging/inflammation can result from pregnancy complications, injuries, menopause, polyps, cancer, infections and the like. In severe cases of hemorrhage or after surgery, vaginal packing is stuffed into the vagina, causing discomfort. Removal of the packing may restart the blood flow. Rectal hemorrhaging/inflammation results from hemorrhoids, ulcers, infections and the like. Current treatments, including steroids and other drugs, may reduce the symptoms, but may not stop the bleeding immediately. Current treatment methods have side effects and do little to address the burning and painful discomfort caused from body cavity hemorrhaging/inflammation. A need exists for a method of treating body cavity hemorrhaging and inflammation that is non-invasive, without side effects, and provides relief for associated symptoms.

SUMMARY OF THE INVENTION

The present invention is a device to treat an overgrowth of yeast in a body cavity comprising a shell, removal means, and a freezable filler contained in a chamber within the shell.

When the filler is frozen and inserted into the body cavity, the shell cools the body cavity to a temperature that prevents the replication of yeast and provides relief to symptoms associated with an overgrowth of yeast by lowering the temperature of the body cavity to a temperature that prevents the replication of the yeast. The filler is any refreezable compound, including but not limited to a liquid, such as saline, distilled water, etc., a gas, and a solid or semi solid, such as a gel.

The chamber may comprise at least two compartments separated by breakable walls Each compartment is each filled with a compound, such that when broken, the compounds create to create a cooling gel. The removal means is any mechanism, such as a string, cord, loop formed in the shell or attached to the shell, tab, and the like, that, when grasped and pulled, removes the device from the body cavity.

In an embodiment, an external cooling component extends from the shell. The external cooling component comprising a component chamber filled with filler, such that when in use, the cooling component extends from the body cavity to provide cooling at the body cavity opening. The external cooling component filler is similar to that in the shell.

In an embodiment useful to treat hemorrhaging/inflammation of a body cavity, the device further comprises a bladder located between an outer wall of the shell and the chamber. The bladder is finable with a filler. The filler in the chamber is frozen. The filler in the bladder is cooled by the filler in the chamber, and may be additionally pre-cooled prior to introducing into the bladder. The filler in the bladder lowers the temperature of the body cavity to promote healing and reduce pain, while the expanded volume provides pressure to control bleeding and swelling for various conditions, including but not limited to post-operative treatment of a body cavity.

As used herein, "approximately" means within plus or minus 25% of the term it qualifies. The term "about" means between ½ and 2 times the term it qualifies.

The compositions and methods of the present invention can comprise, consist of or consist essentially of the essential elements a d limitations of the invention described herein, as well as any additional or optional ingredients, components, or limitations described herein or otherwise useful in compositions and methods of the general type as described herein.

Numerical ranges as used herein are intended to include every number and subset of numbers contained within that range, whether specifically disclosed or not. Further, these numerical ranges should be construed as providing support for a claim directed to any number or subset of numbers in that range or to be limited to the exact conversion to a different measuring system, such, but not limited to, as between inches and millimeters.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

Terms such as "top," "bottom," "right," "left," "above", "under", "side" "front" and "back" and the like, are words of convenience and are not to be construed as limiting.

DETAILED DESCRIPTION

Reference will now be made in detail to the exemplary embodiments of the invention, examples of which are illustrated in the accompanying drawings. In accordance with an embodiment of the present invention.

Figure 1:
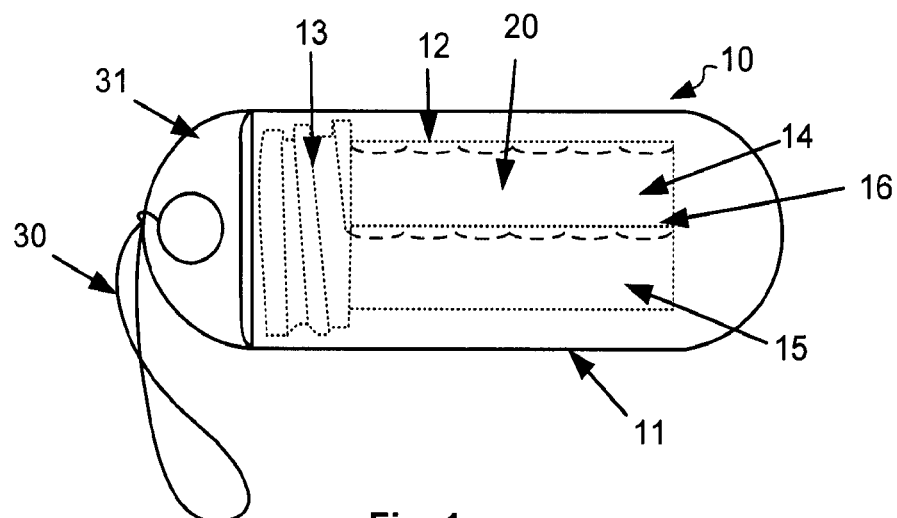
FIG. 1 is a see-through view of an embodiment of the invention showing e chamber for the filler.

As shown in FIG. 1, the device is comprised a shell 10, a filler 20 and removal means 30. The shell is preferably made from silicone and comprises an external wall 11 enclosing a chamber 12 that is sealed with a plug 13. The chamber may have one or more compartments 14, 15. The compartments are formed with breakable wall(s) 16 between or among them. The filler 20 is anon-toxic compound, such as but not limited to, saline, distilled water, a gel, and the like. The tiller may comprise several components that are housed apart in the compartments until use. In an embodiment, the removal means 30 is a string or cord firmly attached to the shell.

Figure 2:
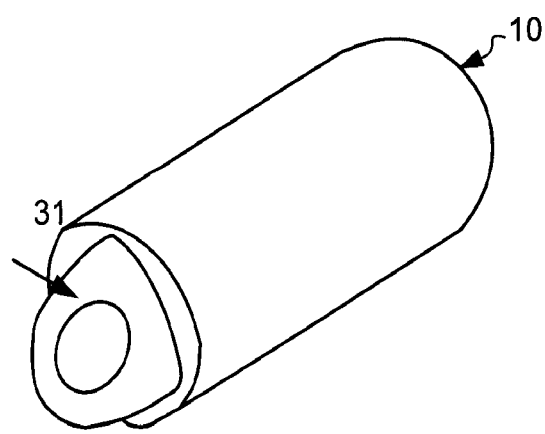
FIG. 2 is a perspective view of an embodiment of the invention.
Figure 3:
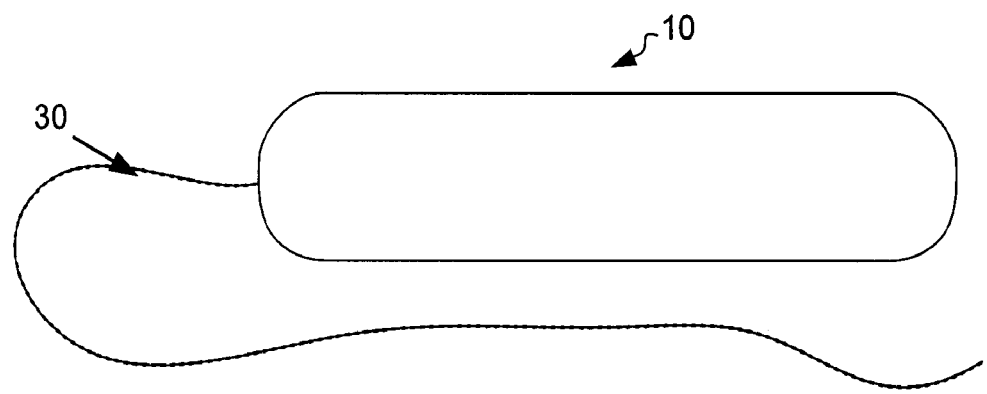
FIG. 3 is a side view of an embodiment of the invention showing a string.
Figure 4:
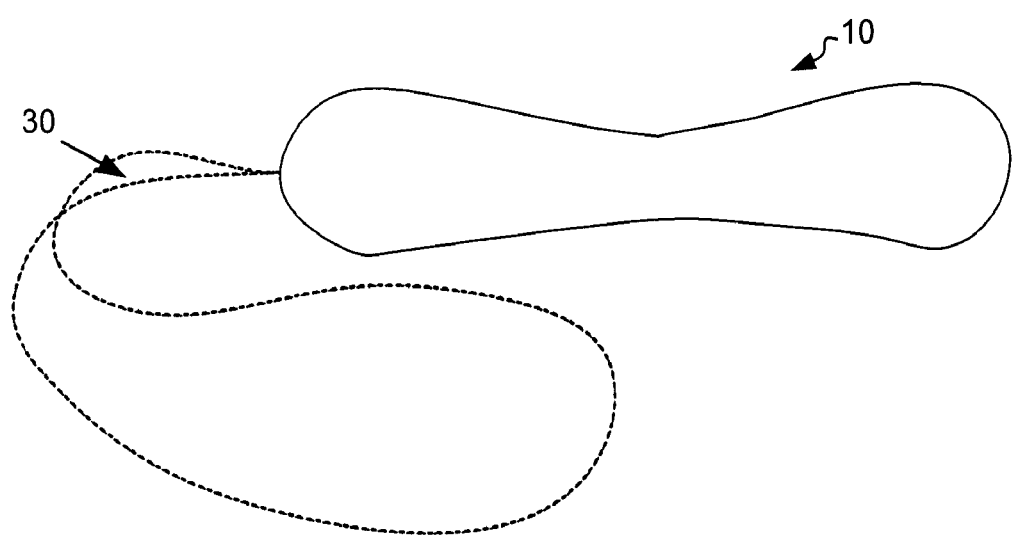
FIG. 4 is a side view of an alternate embodiment of the invention showing looped string.
Figure 5:
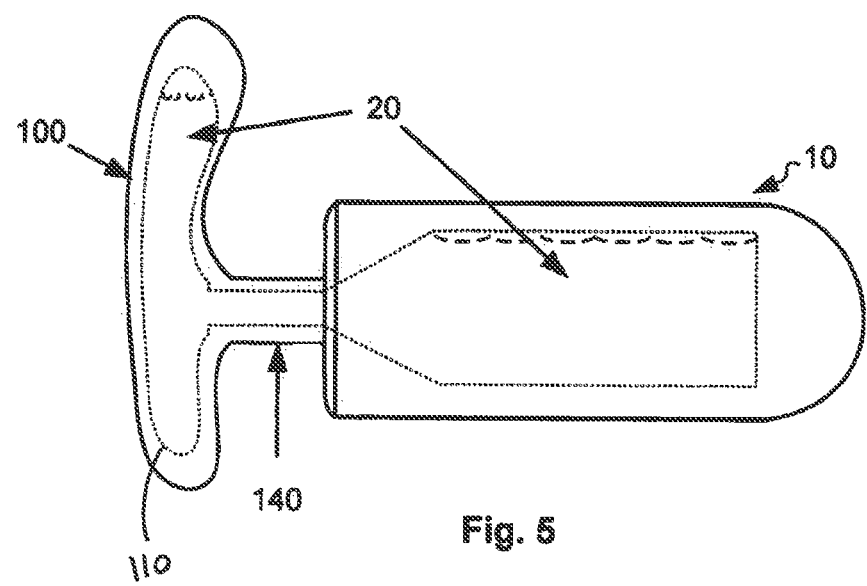
FIG. 5 is a side see-through view of an embodiment of the invention showing the external cooling component.
Figure 6:
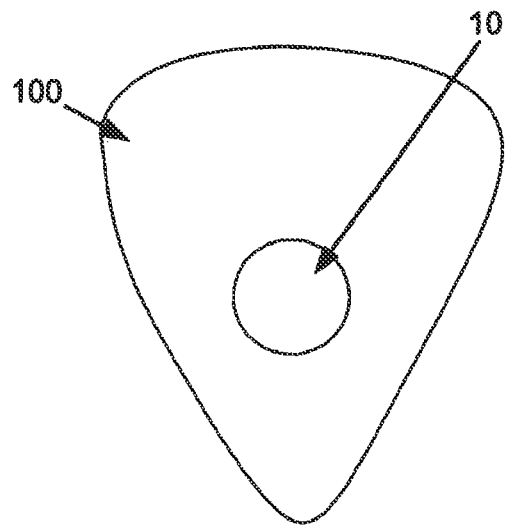
FIG. 6 is atop view of an embodiment e invention showing the external cooling component.

In an embodiment shown in FIG. 2, the removal means comprises an attachment 31. The attachment is an extension of the plug or an extension of the shell that is graspable. In an embodiment, the attachment is a loop formed from silicone. The attachment may comprise an additional removal means, such as a string/cord attached to the ring. In an alternate embodiment shown in FIG. 5 and FIG. 6, the attachment is an external cooling component 100.

The external cooling component extends from the shell at the end closest to the body cavity opening and is external to the cavity opening when in use. In an embodiment, the external cooling component is made of silicone and comprises a component chamber 110 that also may have compartments. The external cooling component is filled with the same filler as the shell chamber, or can be filled with a different cooling compound. The cooling component comprises an extension or neck 140 that connects it to the shell. The neck is flexible so that the external cooling component is positionable against the opening of the body cavity to provide relief to the area around the external opening. In an embodiment, the neck has an internal tube connecting the shell chamber and the component chamber. The chambers may be one body, connectable by breakable walls or separate chambers. In an embodiment, the external cooling component is a disposable removable piece, such as a paper covered gel pack, that attaches to the neck of the shell. While shown in FIG. 6 as a generally triangular shape, the shape of the external cooling component may be anything that adapts to the opening of the body cavity.

Figure 7:
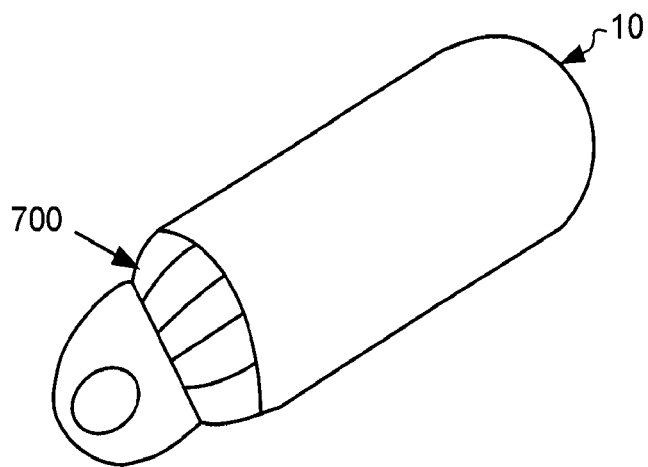
FIG. 7 is a perspective view an alternate embodiment plug.

In an embodiment, the plug 13 is screwed into threads at the opening of the chamber after the filler is inserted. In an alternate embodiment shown in FIG. 7, the plug is has an expandable rounded shoulder 700 that is inserted into the opening of the chamber to seal it.

Figure 8:
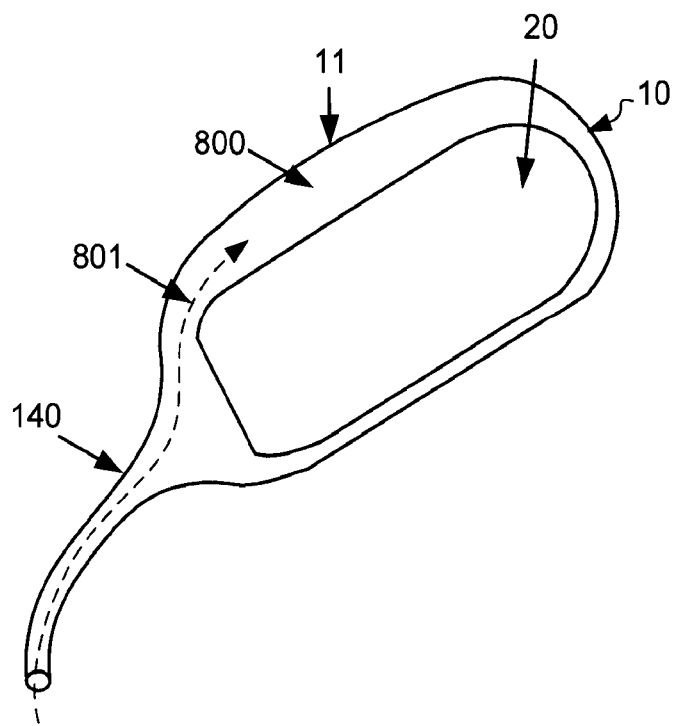
FIG. 8 is a view of an alternate embodiment of the invention used for vaginal bleeding/hemorrhaging.

In an embodiment, the device may be modified for use with body cavity bleeding/hemorrhaging, such as occurring with A-P repair, cystocele/rectocele repairs, episiotomy, vaginal lacerations and repairs, anti-incontinent procedures (trans-vaginal tapes), vaginal hysterectomies, LAVH, hemorrhoid repairs, and the like. As shown in FIG. 8, the neck 140 is an elongated tube that is connected at one end to a port (not shown to infuse and remove filler, such as saline, and at the other end to a bladder 800 located between the wall and the chamber of the shell. The filler flows into the bladder (see arrow 801) and distends the shell (only one side is shown enlarged in the Figure, but one skilled in the art would understand that the filler would enlarge the shell on all side as filler is introduced) to enlarge the device to tamponade body cavity bleeding/hemorrhaging. The amount of saline is selectively introduced to expand the shell slightly or dramatically based on the body cavity and the situation (slight if inflammation and a small body cavity; dramatic if profuse bleeding). The saline is chilled and further cooled by the filler to provide pain relief and reduce swelling to promote healing. The device is easily removed by deflating the saline filled bladder. Additionally, if at the time of deflating the device, bleeding ensues, the device can be refilled to apply the needed pressure to stop the bleeding while the physician decides if further surgery is needed or if an alternate modality is available such as blood products and or radiologic intervention. As such the device provides the advantage of easier placement and removal than typical post-operative packing that may denude tissue on removal or obscure hemorrhage.

The device further comprises abuse and storage container (not shown). The device is packaged in a sterile environment with instructions/explanation of method of use.

The silicone shell is constructed in a various forms. In an embodiment, the shell is of similar fashion to the current silicone breast implants (with regard to thickness of the shell). In an embodiment, the shell is more rigid, similar to silicone used in re-useable ice cubes which are either filled with distilled water or semi-solid silicone gel material. The core or chamber of the device is filled with saline, distilled water, silicone gel or other similar material that can either be frozen or cooled sufficiently to effect a cure of the condition it is designed to treat/cure/or improve. The silicone shell is shaped into a cylinder with varying lengths and circumferences. Visualize a tampon for instance, a bullet, or a hotdog. Also, some of the devices will be shaped with an additional component—visualize a pacifier—to cool the external region of the body cavity. The fourth component will be termed-base. The sizes will be determined by the optimal size to produce the fastest and most comfortable cure. A string of approximately 1-6 inches may be attached to one end of the shell. In a reusable embodiment, the removal means material is compatible with that goal. In a disposable embodiment, the string is any inexpensive method of retrieving or positioning the device from/in the vagina, such as but not limited to, paper, cloth, plastic, or cotton string/cord and the like.

In an embodiment, the invention comprises a covering or shell, a freezable substance inside the shell, and the ability to remove and store the device. Additional mechanism/materials are optional for the purpose of inserting the device. The frozen substance can be liquid, gaseous, semisolid or solid. Additional materials can be used and modifications may be made to the device depending on cost and other considerations.

The silicone or other suitable material used for the shell is a formed into a cylindrical, or tampon-like or hotdog-like shape. In an embodiment, the freezable substance is saline, although any other suitable material or substance may be used. The removal means is sanitizable in nature for reusable devices. In an embodiment, the removal means is a string. In an embodiment, the removal means is a ring or extension of flexible silicone attached to one end of the shell.

Silicone or other suitable material is used as filler for the shell because of the inert properties and proven safety when used inside the body. In manufacturing, the filler is added to the chamber in the shell and the shell is sealed.

As used herein, the words tiller or saline includes any substance or material that can be rendered frozen or sufficiently cold to accomplish the goal of the device. In an embodiment, the filler is a non-toxic polymer gel, such as a food grade gel refrigerant. Saline is distilled water with dissolved sodium chloride (NaCl) or salt. The internal component of the device must be able to made cold, cooler, or frozen when removed from a freezer or analogous device. The device is not frozen at room temperature. Saline or analogous/similar substance/material (when frozen or cold) is the crux of the design of this device. The frozen saline will be the reason that this device is effective and the silicone (or shell material) is malleable and soft enough to be placed in the vagina. Silicone does not freeze when subjected to the temperatures in the common freezer. If the frozen device is too hard or stiff when removed from the freezer, a quick exposure to tap water will soften it. However, the device needs to be in a solid/semi-solid/frozen condition in order for it to be inserted easily.

In an embodiment, the saline is a cold pack encased in the shell having several compartments separated by breakable barriers. Each of the compartments contain an ingredient which, when mixed with the other ingredients, chemically react together to create a cooling effect. For use, the barriers are broken and the contents mixed together.

Alternatively, the saline is an encased instant cold gel pack comprised of Ingredients in breakable compartments, that, when mixed together, form a cooling gel. The addition of the gel allows for later use. For re-use, the device is place in a freezer until needed.

During treatment, the temperature of the membranes of the body cavity near the inserted device drop below about 50° F. and then warm as the filler thaws. The device is effective because it renders the surrounding tissue cooler, and thus the yeast is unable to replicate/reproduce itself and cause the disease, inflammation or condition. The cessation of the overgrowth of yeast allows the body cavities' normal flora to reestablish and suppress the yeast from re-overgrowing when the temperature in the body cavity returns to normal.

The cooling effect will also ameliorate the disturbing symptoms of yeast vaginitis (or other similar conditions). Itching, burning, and swelling respond to coldness by causing the capillaries to shrink (constrict) thus preventing the egress of a fluid into the tissue which results in swelling and pain. Coldness/ice packs are effective ways to reduce swelling caused by inflammation. Saline/silicone gel, or distilled water will remain in the solid state longer than tap water and will freeze more quickly that water. Also, saline, silicone gel, and distilled water are sterile and safe.

The process would be similar to the production of saline filled silicone breast implants and/or re-useable ice cubes (made of a silicone shell), with the addition of a flexible string-loop-like material for easy removal of the device. If the device is not to be a reusable device, then the string could be the same as a tampon (i.e. cotton).

Other substances can be used to fabricate this device such as using a tampon-like material and not using an enclosure (shell) like the silicone capsule (shell). However, any absorbent material will result in moisture being introduced and wetness will make this unsuitable for most women (besides aggravating the condition it was designed to treat), including latex or other rubber/plastic materials, if not a substance that causes allergic reactions.

The device may be used in other body cavities, such as the rectum, when an overgrowth of yeast creates symptoms similar to vaginitis, or for symptomatic hemorrhoids, whether bleeding or not, and for intraoperative or postoperative bleeding during rectal/anal procedures/surgeries.

A person would keep the device(s) in a frozen state until needed. Then, the device would be removed from the storage container and placed under tap water for 3-5 seconds or less, then inserted into the body cavity (vagina or analogous body cavity, i.e. rectum/anus). The rounded end is inserted first, so that the removal means is closest to the body cavity opening. The device may be adjusted using the attachment or the removal means for comfort. The device remains in the body cavity for approximately 1 hour or until no additional cooling sensation is noticed/experienced, and is then removed. A subsequent frozen device would be inserted at that time, if needed. This could be continued until the person was not experiencing any itching or discomfort, possibly requiring 2-4 hours of treatment or 2-3 sequentially used intravaginal devices, depending on the severity of the symptoms. Once the device has been used, it is removed, rinsed in warm, soapy water, dried and replaced back in the storage container in the freezer.

The invention treats a condition called vaginitis—caused by yeast (all genus/species or yeast, specifically, *Candida albicans, Candida-torulopsis*, and *Candida glabarata*) and may be effective against other microbes, such as protozoa and bacteria. It solves the problem by lowering the temperature in the vagina thus limiting the growth of yeast, bacteria, and other microbes. It also ameliorates the concomitant symptoms such as burning and itching and swelling.

The foregoing descriptions of specific embodiments and examples of the present invention have been presented for purposes of illustration and description. They are not intended to be exhaustive or to limit the invention to the precise forms disclosed, and obviously many modifications and variations are possible in light of the above teachings. It will be understood that the invention is intended to cover alternatives, modifications and equivalents. The embodiments were chosen and described in order to best explain the principles of the invention and its practical application, to thereby enable others skilled in the art to best utilize the invention and various embodiments with various modifications as are suited to the particular use contemplated. It is therefore to be understood that within the scope of the appended claims, the invention may be practiced otherwise than as specifically described herein.

I claim:

1. A device for insertion in a vaginal of a user to inhibit growth of yeast therein, comprising:
    a shell having a wall that encloses a chamber formed therein, the shell further having a plug that seals the chamber closed, the shell formed from a flexible expandable polymer that is sized and adapted for intimate contact with walls of the vagina; and
    a cooling filler material that substantially fills the chamber, the cooling filler material selected to cool the walls of the vagina in contact with the shell;
    wherein upon filling the chamber with the cooling filler material the flexible expandable polymer is capable of expanding and wherein upon removing the cooling filler material the flexible expandable polymer is capable of passively returning to its original shape; and wherein upon contact with walls of the vagina the flexible expandable polymer is capable of flexing, and wherein the device does not include a second chamber for enclosing or accepting any additional contents, and wherein the cooling filler material does not circulate into or out of the chamber when the chamber is closed and is capable of being removed from or added to the chamber when the chamber is opening to refill the device for reuse;
    wherein the cooling filler material is at least one of saline, distilled water, and a gel.

2. The device of claim 1, further comprising:
    a means, attached to the shell, for removing the device from the vagina by grasping.

* * * * *